United States Patent

Gibbs et al.

[11] Patent Number: 5,752,658
[45] Date of Patent: May 19, 1998

[54] AIR FRESHENER AND CHAIN PULL DEVICE FOR CEILING FAN

[75] Inventors: George S. Gibbs, Thomasville; James T. Baxter, Hahira; Douglas M. Vick, Thomasville, all of Ga.

[73] Assignee: New Ideas International, Inc., Thomasville, Ga.

[21] Appl. No.: 689,460

[22] Filed: Aug. 8, 1996

Related U.S. Application Data

[63] Continuation-in-part of Ser. No. 518,800, Aug. 24, 1995.

[51] Int. Cl.⁶ ............................................. A61L 9/04
[52] U.S. Cl. ............................. 239/56; 239/57; 239/289; 220/4.21; 220/4.24
[58] Field of Search ................... 239/53, 56, 57; 222/570; 220/4.21, 4.24, 780, 784, 794

[56] References Cited

U.S. PATENT DOCUMENTS

| | | | |
|---|---|---|---|
| D. 247,249 | 2/1978 | Schimanski | D23/150 |
| 2,755,954 | 7/1956 | Antritter | 239/57 X |
| 3,844,478 | 10/1974 | Davis | 239/57 |
| 4,219,145 | 8/1980 | Jaeschke et al. | 229/8 |
| 4,360,118 | 11/1982 | Stern | 220/4.24 |
| 4,361,279 | 11/1982 | Beacham | 239/56 |
| 4,630,775 | 12/1986 | Mandon et al. | 239/56 |
| 4,753,573 | 6/1988 | McKnight | 416/62 |
| 4,889,543 | 12/1989 | Burt | 55/97 |
| 4,944,898 | 7/1990 | Glaser | 261/84 |
| 4,960,240 | 10/1990 | McElfresh | 239/56 |
| 5,022,819 | 6/1991 | Murcin et al. | 416/62 |
| 5,377,860 | 1/1995 | Littlejohn et al. | 220/4.21 X |

OTHER PUBLICATIONS

Windscent rack card, 1995, RWL Corp.

*Primary Examiner*—Andres Kashnikow
*Assistant Examiner*—Steven J. Ganey
*Attorney, Agent, or Firm*—Kennedy, Davis & Kennedy

[57] ABSTRACT

An air freshener device disposed in proximity to a ceiling fan by attachment to a pull chain of the ceiling fan for scenting air moved by the fan. The device receives a scented pad in a first dish that defines a pair of opposite slots for receiving links of the pull chain for securing the device in close proximity to the ceiling fan and for overlying the scented pad in the first dish. A second dish joins to the first dish by engaging a flange on the second dish to a groove in the first dish. The groove is defined by a rib which extends outwardly of a thinner distal portion of the skirt and a thicker portion of the skirt. The dishes define a plurality of vent openings for exposing the scented pad to air moved by the ceiling fan. A first tab extends outwardly of the first dish and a second tab extends outwardly of the second dish in partially overlapping relation, whereby the joined dishes are separated by twistingly moving the tabs in opposite directions.

1 Claim, 3 Drawing Sheets

AIR FRESHENER AND CHAIN PULL DEVICE FOR CEILING FAN

This application is a continuation-in-part of co-pending application Ser. No. 08/518,800 filed Aug. 24, 1995.

TECHNICAL FIELD

The present invention relates to ceiling fans. More particularly, the present invention relates to devices for scenting air moved by ceiling fans.

BACKGROUND OF THE INVENTION

Ceiling fans have become popular additions to rooms of homes and restaurants, in part for decoration and in part for economical movement of air for both cooling and heating seasons. The ceiling fans typically have an electric motor that mounts to a bracket rigidly connected to the ceiling. A plurality of fan blades attach to a rotatable ring that is operatively coupled to the electric motor. The fan blades generally mount at an acute angle relative to horizontal, for pushing air on the surfaces of the blades as the motor rotates the ring. During warm weather, the fans rotate in a first direction to push air downwardly upwardly towards the floor in order to induce circulation of the cooler air near the floor. During cold weather, the fans rotate in a second opposite direction to push air upwardly towards to the ceiling in order to induce circulation of the warmer air near the ceiling. The circulation of air creates a desirable cooling or warming effect.

In addition to use of ceiling fans to circulate air, the use of devices that emit an air scenting fragrance has increased. Releasing fragrance in to ambient air has the effect of deodorizing and freshening the air. Often such devices have housings for positioning the scent emissive material statically in a room. Other devices warm a scented material to induce the fragrance in to the air of a room. The scented material typically comprises an evaporative solid or liquid.

While these scent emissive devices have accomplished the scenting of air, there are problems associated with their use. In particular, the scent emissive devices often are placed away from moving air, such as adjacent a wall socket near a floor or on a shelf adjacent a side wall of the room. The devices thereby are less directly exposed to moving air and contact relatively static air. The distribution of scent is thereby limited and reduces the effectiveness of the scenting for a room.

It is thus seen that a need exists for an improved scent-emissive device for disposing in proximity to ceiling fans for scenting air placed in motion by the fans. It is to the provision of such that the present invention is primarily directed.

SUMMARY OF THE INVENTION

The present invention comprises an air freshener apparatus for engagement to a pull-chain of a ceiling fan for scenting air moved by the ceiling fan. The apparatus has a first dish defined by a plate and a skirt extending laterally from a perimeter edge of the plate. The plate and the skirt define a recess for receiving a pad having a scented residue deposited therein for scenting the air. The skirt defines a first portion adjacent the plate and a distal portion which has a thickness thinner than that of the first portion. A rib extends outwardly from the exterior surface of the distal portion intermediate the first portion and a distal edge of the skirt, and thereby defines a groove between the rib and an edge of the first portion of the skirt. The skirt further defines a pair of oppositely aligned slots for receiving links of the pull chain of the ceiling fan for overlying the scented pad received in the first dish. A tab extends outwardly from an exterior surface of the first portion of the skirt. The plate defines a plurality of vent openings for communicating air to the scented pad.

The first dish connects to a second dish after securing the scented pad therein. The second dish has a plate and a skirt that extends laterally from a perimeter edge of the plate. A flange extends outwardly from an interior surface at a distal edge of the skirt for engaging the groove in the first dish. The skirt further defines a pair of oppositely aligned notches for conformingly receiving portions of the pull chain. A second tab extends outwardly from an exterior surface of skirt. The second tab partially overlaps the first tab. The plate defines a plurality of vent openings for communicating air to the scented pad.

The first dish and the second dish are engaged together by aligning the facing skirts together and engaging the flange in the groove. The ceiling fan moves air past the scent pad exposed in the vent openings. The dishes are separated for replacing the scent pad by twistingly moving the first tab and the second tab in opposite directions to disengage the flange from the groove.

DETAILED DESCRIPTION

Figure 1:
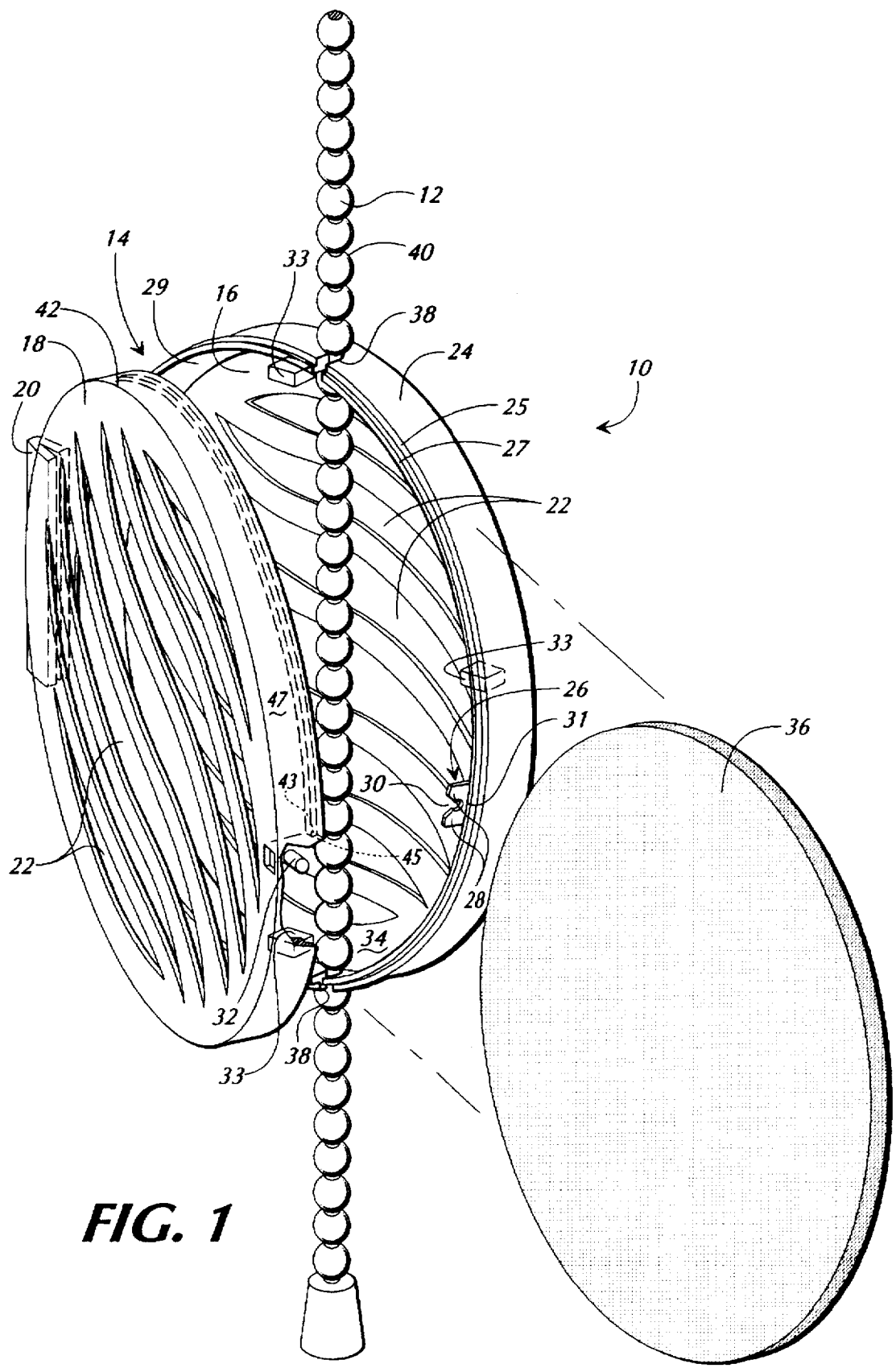
FIG. 1 is a perspective view of an air freshening device for holding a scent-emissive pad in proximity to a ceiling fan according to the present invention.
Figure 2:
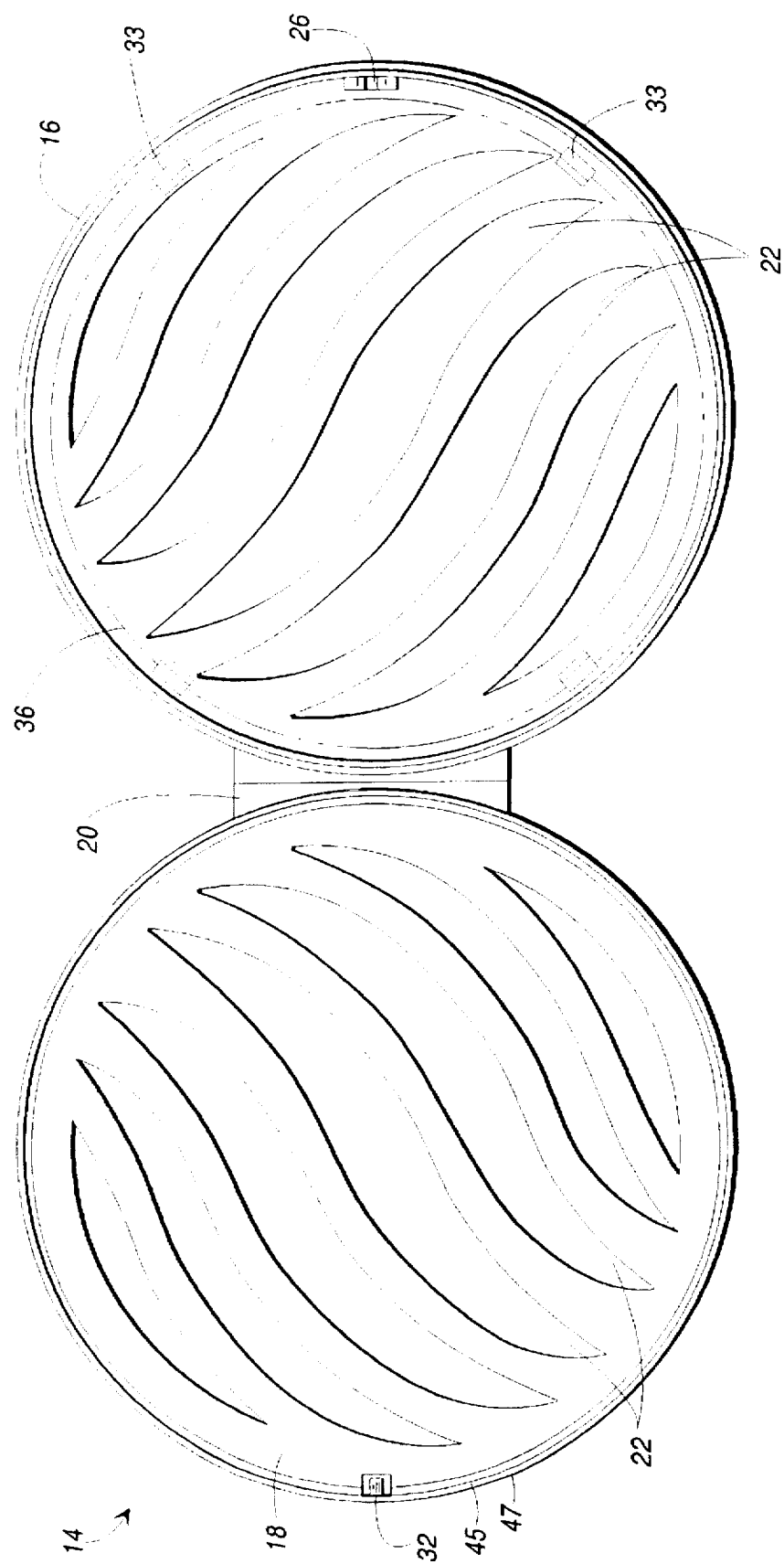
FIG. 2 is a plan view of the air freshening device illustrated in FIG. 1.

Referring now in more detail to the drawings which illustrate an air freshener device 10 for engagement to a pull-chain 12 of a ceiling fan (not illustrated). The air freshener apparatus 10 comprises a unitary clam-shell housing 14 having a first dish 16 and a second dish 18 joined together by an intermediate foldable hinge 20. Each dish 16 and 18 defines a plurality of vent openings 22 for passage of air therethrough. A skirt 24 extends laterally a predetermined distance from the dish 16 around a perimeter edge. A distal edge of the skirt 24 defines a recessed notch 25 wherein the thickness of the outwardly extending wall 27 is of a reduced thickness relative the thickness of the skirt. In the illustrated embodiment, the wall 27 is collinear with an inner face 29 of the skirt 24. A latch member 26 extends laterally from the first dish 16 on the skirt 24. A pair of arms 28 extend outwardly at an angle and define a channel 30 for receiving a post 32 into a notch 31.

The dish 16 includes a plurality of locating ribs 33 that are upstanding from an interior surface 34 for guidingly locating edges of a scented pad 36 received therein. A pair of oppositely aligned slots 38 in portions of the skirt 24 of the first dish 16 receive links 40 of the pull-chain 12 of the ceiling fan. The pull chain 12 thereby overlies the scented pad 36 in the first dish 16 for securing the scented pad therein.

A skirt 42 extends laterally a predetermined distance from the dish 18 around a perimeter edge. A distal edge of the skirt 42 defines a recessed notch 43 wherein the thickness of the outwardly extending wall 45 is of reduced thickness relative the thickness of the skirt 42. The wall 45 in the illustrated embodiment is collinear with an outer face 47 of the skirt 42. The notches 25 and 43 matingly engage when the clam shell dishes 16 and 18 are closed together, as discussed below. The notches 25 and 43 are preferably one-half the thickness of the skirts 24 and 42. The post 32 extends radially inwardly from the skirt 42 of the dish 18. The post 32 is aligned on the skirt 42 with respect to the latch member 26 on the skirt 24 for being received through the channel 30 and into the notch 31 upon folding the dishes 16 and 18 together along the hinge 20.

In use, the housing 10 holds the scent-emissive pad 36 and connects to the chain 12 of the ceiling fan. In a preferred embodiment, the scent-emissive pad comprises a foam substrate that holds a carrier material and an evaporative fragrance. The carrier material and evaporative fragrance preferably are homogeneously blended together and applied to the foam substrate. The air freshening device is preferably molded of a resilient plastic material. The scented pad 36 is positioned in the first dish 16 juxtaposed to the locating ribs 33 that abut the edges of the pad. The locating ribs 33 guide the placed of the scented rib 36 in the first dish 16. A portion of the pull-chain 12 is slippingly engaged to one of the slots 38 in the first dish 16 by introducing one of the links 40 into the slot. The pull chain 12 overlies the scented pad 36, and a second portion of the pull-chain is slippingly engaged to the second slot in the dish 16. The dishes 16 and 18 are then closed together by folding the device 10 on the hinge 20. This brings the post 32 into the channel 30 which guides the post into engagement with the notch 31, thereby locking the clam-shell housing 14 together. The air freshening device 10 then hangs a short distance below the ceiling fan in proximity of air circulated by the fan.

The openings 22 in the dishes 16 and 18 allow air circulated by the ceiling fan to contact the scent-emissive pad 36. The evaporative fragrance migrates through the carrier pad 36 to its surfaces where the circulating air becomes scented by passing in contact with the pad. The housing 14 is securely held to the pull chain 12 by the slots 38. The ceiling fan thereafter can be operated by grasping the air freshening device 10 in order to pull the chain 12 to operate the ceiling fan.

Figure 3:
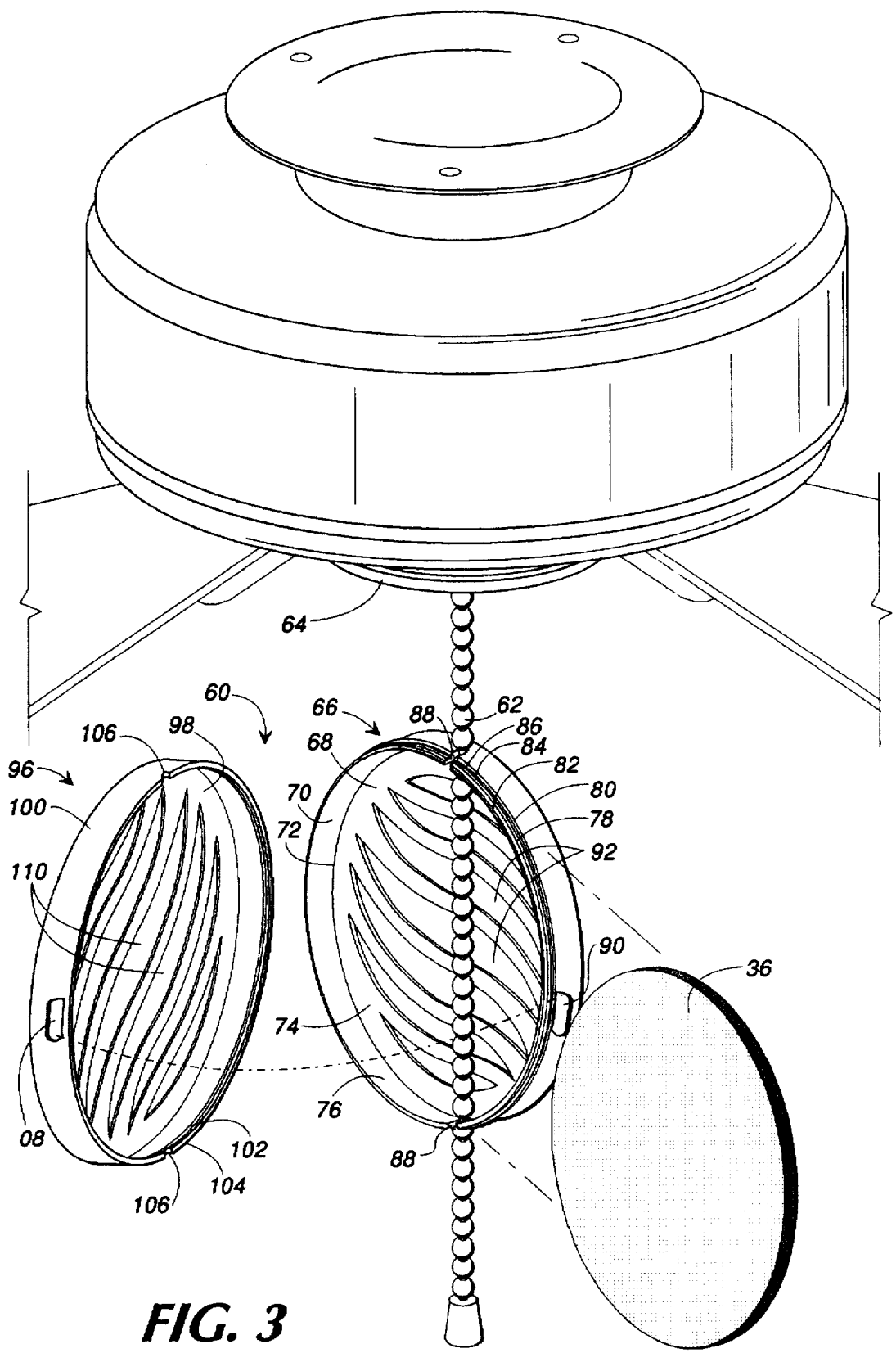
FIG. 3 is a perspective view of an air freshening device for holding a scent-emissive pad in proximity to a ceiling fan according to the present invention.

FIG. 3 illustrates an air freshener apparatus 60 for engagement to a pull-chain 62 of a ceiling fan 64. The apparatus 60 comprises a first dish 66 defined by a plate 68 and a skirt 70 extending laterally from a perimeter edge 72 of the plate 68. The plate 68 and the skirt 70 define a recess 74 for receiving the pad 36 having a scented residue deposited therein for scenting the air. The skirt 70 defines a first portion 76 adjacent the plate 70 and a distal portion 78 which has a thickness thinner than that of the first portion 76. A rib 80 extends outwardly from the exterior surface of the distal portion 78 intermediate the first portion 76 and a distal edge 82 of the skirt 70, and thereby defines a groove 84 between the rib 80 and an edge 86 of the first portion 76 of the skirt 70. The skirt 70 further defines a pair of oppositely aligned slots 88 for receiving link segments of the pull chain 62 of the ceiling fan 64 for overlying the scented pad 36 received in the first dish 66. A tab 90 extends outwardly from an exterior surface of the first portion of the skirt 70. The plate 68 defines a plurality of vent openings 92 for communicating air to the scented pad 36.

The first dish 66 connects to a second dish 96 after receiving the scented pad 36 therein. The second dish 96 similarly has a plate 98 and a skirt 100 that extends laterally from a perimeter edge of the plate 98. A flange 102 extends outwardly from an interior surface at a distal edge 104 of the skirt 100 for engaging the groove 84 in the first dish 66. The skirt 100 further defines a pair of oppositely aligned notches 106 for conformingly receiving link segments of the pull chain 62. A second tab 108 extends outwardly from an exterior surface of the skirt 100. The second tab 108 partially overlaps the first tab 90 when the first dish 66 and the second dish 96 are matingly engaged for a purpose discussed below. The plate 98 defines a plurality of vent openings 110 for communicating air to the scented pad 36.

The apparatus 60 is secured to the pull chain 62 of the ceiling fan 64 with the scented pad 36 for scenting air moved by the ceiling fan. The scented pad 36 is first disposed in the recess 74. The pull chain 62 is then engaged to the slots 88 which receive links of the pull chain. One of the links in the pull chain 62 is slidingly received by one of the slots 88. The pull chain 62 overlies the scent pad 36 and extends towards the other of the pair of slots 88. Another of the links in the pull chain 62 is received in the other slot 88. The pull chain 62 overlies the scented pad 36 and secures the scented pad 36 within the recess 74. It is noted here that the apparatus 60 is readily engaged to a pull chain for a light fixture, which commonly are suspended from ceiling fans.

The first dish 66 and the second dish 96 are then engaged together by aligning the facing skirts 70 and 100 together and engaging the flange 102 in the groove 84. The ceiling fan is then operated to circulate air past the scent pad 36 exposed in the vent openings 92 and 110. The evaporative fragrance in the scent pad 36 migrates through the pad to the surface for being exposed to the circulating air, and thereby scenting the air in a room.

After the scent in the pad 36 is spent, the dishes 66 and 96 are separated for replacing the scent pad. The dishes are separated by twistingly moving the first tab 90 and the second tab 108 in opposite directions to disengage the flange 102 from the groove 84. This is accomplished by positioning a thumb of a hand on an inside face of the tab 108 and a forefinger of the hand of an inside face of the tab 90, and twistingly moving the tabs apart.

Further, the apparatus 60 can be grasped and moved to pull the pull chain 62 and thereby operate the ceiling fan. The dishes 66 and 96 are preferably molded of a fragrance-resistant plastic material, such as polypropylene or high density polyethylene. In an alternate embodiment, (not illustrated) the dishes 66 and 96 are integrally engaged together by a hinge. The present invention is useful with the scent pad 36 discussed above. However, the invention is useful with other fragrance-bearing substrates, such as molded plastic or scent emittive resins.

The foregoing has disclosed improved air freshener and chain puller devices for operating ceiling fans and scenting the air moved thereby. It should be understood that the above described embodiments merely illustrate principles of the invention in preferred forms. Many modifications, additions, and deletions may, of course, be made thereto without departure from the spirit and scope of the invention as set forth in the following claims.

What is claimed is:

1. An air freshener apparatus for engagement to a pull-chain of a ceiling fan, comprising:
   a first dish having a plate and a skirt extending a predetermined distance laterally from a perimeter edge of the plate, said plate and said skirt defining a recess for receiving a pad having a scented residue deposited therein, said skirt defining a first portion adjacent the plate and a distal portion, the distal portion of said skirt having a thickness thinner than that of the first portion, a rib extending outwardly from the exterior surface of the distal portion intermediate the first portion and a distal edge of the skirt and defining a groove between said rib and an edge of the first portion of said skirt, said skirt further defining a pair of oppositely aligned slots for receiving segments of a pull chain of a ceiling fan for overlying a scented pad received in the dish, a tab extending outwardly from an exterior surface of the first portion of the skirt, the plate defining a plurality of vent openings for communicating air therethrough;

a second dish having a plate and a skirt extending a predetermined distance laterally from a perimeter edge of the plate, a flange extending outwardly from an interior surface at a distal edge of the skirt for engaging said groove in said first dish, said skirt further defining a pair of oppositely aligned notches for conformingly receiving portions of the pull chain, a second tab extending outwardly from an exterior surface of the skirt and disposed for partial overlapping alignment with said first tab, the plate defining a plurality of vent openings for communicating air therethrough;

whereby the first dish and the second dish, being engaged together upon aligning the facing skirts together and engaging the flange in the groove with air moved by the ceiling fan past the scent pad exposed in the slotted openings being scented thereby, are separated for replacing the scent pad by moving the first tab and the second tab in opposite directions to disengage the flange from the groove.

\* \* \* \* \*